United States Patent
Easley

(10) Patent No.: US 10,219,941 B2
(45) Date of Patent: *Mar. 5, 2019

(54) SYSTEMS AND METHODS FOR VITRECTOMY

(71) Applicant: Synergetics, Inc., O'Fallon, MO (US)

(72) Inventor: James C. Easley, Cottleville, MO (US)

(73) Assignee: SYNERGETICS, INC., O'Fallon, MO (US)

(*) Notice: Subject to any disclaimer, the term of this patent is extended or adjusted under 35 U.S.C. 154(b) by 145 days.

This patent is subject to a terminal disclaimer.

(21) Appl. No.: 15/170,564

(22) Filed: Jun. 1, 2016

(65) Prior Publication Data

US 2016/0270957 A1 Sep. 22, 2016

Related U.S. Application Data

(63) Continuation of application No. 13/944,666, filed on Jul. 17, 2013, now Pat. No. 9,381,113, which is a
(Continued)

(51) Int. Cl.
*A61F 9/007* (2006.01)
*A61B 50/31* (2016.01)

(52) U.S. Cl.
CPC .......... *A61F 9/00763* (2013.01); *A61B 50/31* (2016.02); *A61F 9/00736* (2013.01); *F04C 2270/041* (2013.01)

(58) Field of Classification Search
CPC .. A61F 9/00763; A61F 9/00736; A61B 50/31; A61B 2017/00544; A61B 17/320068
See application file for complete search history.

(56) References Cited

U.S. PATENT DOCUMENTS

| 4,274,411 A | 6/1981 | Dotson, Jr. |
| 4,696,298 A | 9/1987 | Higgins |

(Continued)

FOREIGN PATENT DOCUMENTS

EP 0316085 5/1989

OTHER PUBLICATIONS

European Extended Search Report, EP12797540, dated Nov. 18, 2014 (4 pages).
(Continued)

*Primary Examiner* — Tuan V Nguyen
(74) *Attorney, Agent, or Firm* — Nixon Peabody LLP

(57) ABSTRACT

A system for conducting a vitrectomy includes: a gas source; a vitrector including a cutting mechanism that opens and closes according to a pressure at the vitrector; and a pulse-generating system receiving gas from the gas source and generating pulses at the vitrector. The pulses cause the pressure at the vitrector to vary according to a cycle, and the varying pressure at the vitrector causes the cutting mechanism of the vitrector to open and close. At a first time in the cycle, the pulse-generating system, raises the pressure at the vitrector to a maximum pressure. At a second time in the cycle, the pulse-generating system reduces the pressure at the vitrector to a minimum pressure that is greater than ambient, the pressure at the vitrector being maintained at least at the minimum pressure. The difference between the maximum pressure and minimum pressure is minimized to reduce gas consumption.

17 Claims, 11 Drawing Sheets

Related U.S. Application Data continuation of application No. 13/153,912, filed on Jun. 6, 2011, now Pat. No. 8,496,681.

(56) References Cited

U.S. PATENT DOCUMENTS

| | | |
|---|---|---|
| 5,176,628 A | 1/1993 | Charles |
| 5,417,246 A | 5/1995 | Perkins |
| 5,857,485 A | 1/1999 | Perkins |
| 6,383,203 B1 | 5/2002 | Makihara |
| 6,514,268 B2 | 2/2003 | Finlay |
| 6,575,990 B1 | 6/2003 | Wang |
| 6,773,445 B2 | 8/2004 | Finlay |
| 8,496,681 B2 | 7/2013 | Easley |
| 2007/0078359 A1 | 4/2007 | Luloh |
| 2008/0103433 A1 | 5/2008 | Nazarifar |
| 2008/0149197 A1 | 6/2008 | Turner |
| 2009/0082715 A1 | 3/2009 | Charles |
| 2010/0145374 A1 | 6/2010 | Perkins |
| 2011/0144675 A1 | 6/2011 | Gao |
| 2011/0295293 A1 | 12/2011 | Agahi |

OTHER PUBLICATIONS

International Search Report for International Application No. PCT/2012/040836, dated Oct. 26, 2012 (3 pages).

ABSTRACT# SYSTEMS AND METHODS FOR VITRECTOMY

This application is a continuation of U.S. patent application Ser. No. 13/944,666, filed Jul. 17, 2013, now U.S. Pat. No. 9,381,113, which is a continuation of U.S. patent application Ser. No. 13/153,912, filed Jun. 6, 2011, now U.S. Pat. No. 8,496,681, each of which is hereby incorporated by reference herein in its entirety.

BACKGROUND OF THE INVENTION

Field of the Invention

The invention pertains to vitrectomy, and more particularly, to portable systems and methods that allow vitrectomy to be conducted in a wide variety of clinical environments.

Description of Related Art

Vitrectomy is the surgical removal of vitreous gel from the middle of the eye. Vitreous gel (also called vitreous humor) is a thick, colorless, gel-like fluid that fills the large space in the middle of the eye, behind the lens. Vitreous gel helps the eyeball maintain its shape.

Removal of the vitreous gel, in some cases, provides better access to the back of the eye for particular treatments. For example, vitrectomy provides access for repairing or preventing traction retinal detachment, repairing very large tears in the retina, or treating severe proliferative retinopathy. Vitrectomy may also be employed to reduce vision loss caused by severe or prolonged bleeding in the vitreous gel (vitreous hemorrhage).

Vitrectomy involves three functions: cutting, suction, and infusion. During vitrectomy, small incisions are made in the wall of the eye, through which various instruments are passed. In particular, the doctor inserts a working instrument, e.g., a vitrector, into the eye, cuts the vitreous gel, and suctions the vitreous gel out. A vitrector combines a guillotine style cutting mechanism with vacuum suction. When suction is initiated, the vitreous gel is drawn through a port in the probe tip and then severed by the cutting mechanism. In addition, saline is infused into the eyeball to keep the eyeball distended for treatment. After removing the vitreous gel, the surgeon may treat the retina with a laser (photocoagulation), cut or remove fibrous or scar tissue from the retina, flatten areas where the retina has become detached, or repair tears or holes in the retina or macula. At the end of the surgery, saline, silicone oil, or a gas is injected into the eye to replace the vitreous gel and restore normal pressure in the eye.

Vitrectomies are typically conducted in facilities dedicated to surgical procedures, such as an operating room in a hospital. Special power and gas systems are generally available in such environments. These systems are usually monitored by various computerized alarm systems. In particular, hospitals employ highly controlled power systems that provide uninterrupted electricity throughout the hospital. Furthermore, hospitals employ piped gas systems that supply pressurized oxygen, nitrous oxide, nitrogen, carbon dioxide, and/or clean outside air via pipes to operating rooms and other parts of the hospital. Because vitrectomies are typically conducted in hospital facilities, conventional vitrectomy systems are designed to rely on the special power and gas systems available in such facilities. For example, conventional vitrectomy systems that employ gas-driven vitrectors can be simply connected to a gas port readily available in a hospital operating room to receive the pressurized gas needed for driving the vitrector. Accordingly, conventional vitrectomy systems cannot be easily implemented in facilities without special systems that effectively provide unlimited power and pressurized gas.

SUMMARY OF THE INVENTION

In view of the foregoing, aspects of the present invention provide systems and methods that allow vitrectomy to be conducted in a wide variety of clinical environments. Advantageously, embodiments according to aspects of the present invention do not rely on special power and gas systems that are typically only available in special hospital facilities. Thus, such embodiments may be implemented in doctors' offices, which may not have access to special systems that provide power and/or gas.

For example, aspects of the present invention use gas more efficiently so that the vitrectomy system can use widely available and smaller gas cylinders. According to one embodiment, a system for conducting a vitrectomy includes: a gas source; a vitrector including a cutting mechanism that opens and closes according to a pressure at the vitrector; and a pulse-generating system receiving gas from the gas source and generating pulses at the vitrector. The pulses cause the pressure at the vitrector to vary according to a cycle, and the varying pressure at the vitrector causes the cutting mechanism of the vitrector to open and close. At a first time in the cycle, the pulse-generating system raises the pressure at the vitrector to a maximum pressure. At a second time in the cycle, the pulse-generating system reduces the pressure at the vitrector to a minimum pressure that is greater than ambient, the pressure at the vitrector being maintained at least at the minimum pressure. By employing a minimum pressure greater than ambient, the difference between the maximum pressure and minimum pressure is minimized to reduce gas consumption.

Correspondingly, a method for vitrectomy includes: providing a pulse-generating system with gas from a gas source; and generating pulses from the pulse-generating system at a vitrector. The vitrector includes a cutting mechanism. The pulses cause the pressure at the vitrector to vary according to a cycle, and the varying pressure at the vitrector causes the cutting mechanism of the vitrector to open and close. The act of generating pulses includes: raising, at a first time in the cycle, the pressure at the vitrector to a maximum pressure, and reducing, at a second time in the cycle, the pressure at the vitrector to a minimum pressure that is greater than ambient, the pressure at the vitrector being maintained at least at the minimum pressure.

Additional aspects of the invention will be apparent to those of ordinary skill in the art in view of the detailed description of various embodiments, which is made with reference to the drawings, a brief description of which is provided below.

DETAILED DESCRIPTION

Aspects of the present invention provide systems and methods that allow vitrectomy to be conducted in a wide variety of clinical environments. Advantageously, embodiments according to aspects of the present invention do not rely on special power and gas systems that are typically only available in special hospital facilities. Thus, such embodiments may be implemented in doctors' offices, which may not have access to special systems that provide unlimited power and/or gas.

Figure 1:
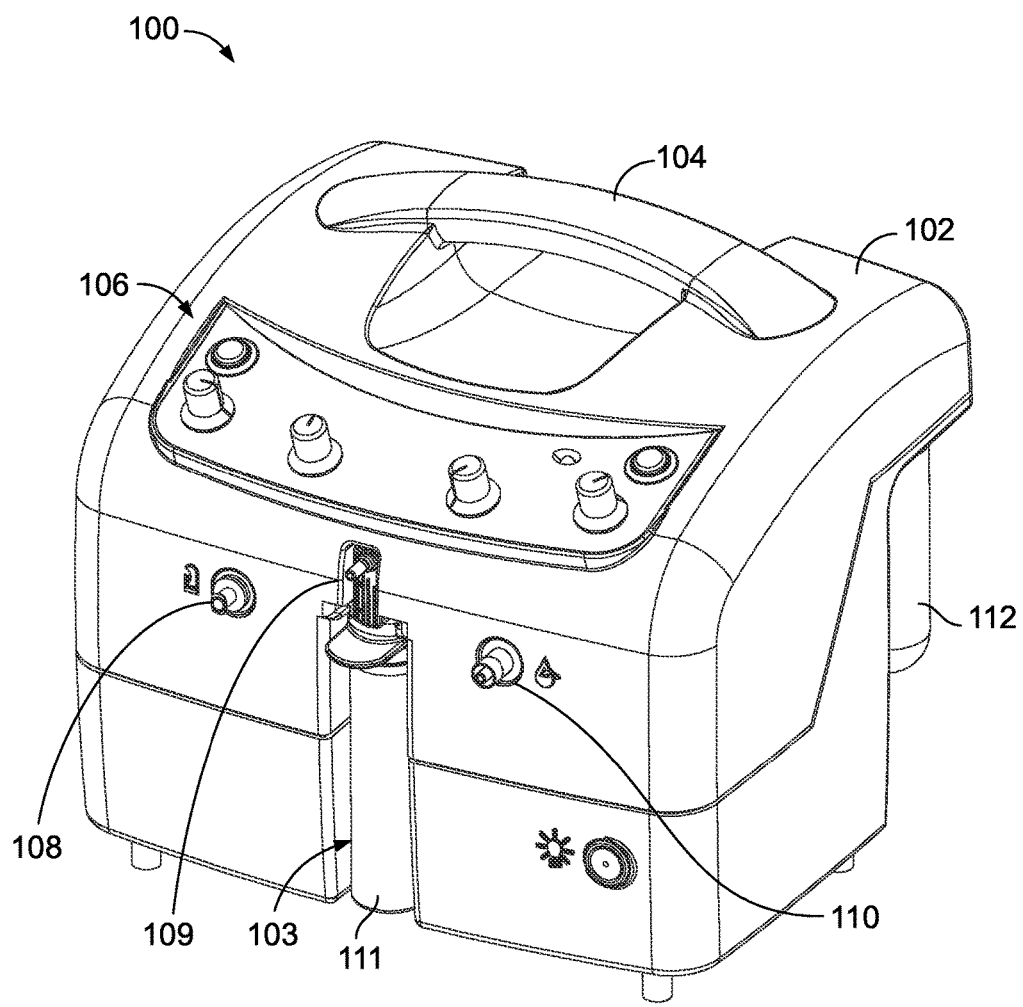
FIG. 1 illustrates an example vitrectomy system according to aspects of the present invention.

Aspects of the present invention provide systems and methods for driving a vitrector, providing aspiration, and/or handling fluid-air exchange in a vitrectomy system. Referring to FIG. 1, an example vitrectomy system 100 is illustrated. Components of the vitrectomy system 100 are assembled into an apparatus defined by a housing 102. As shown in FIG. 1, the housing 102 includes a handle 104 to make the vitrectomy system 100 more easily portable. Advantageously, the vitrectomy system 100 is sized for portability and is not restricted to a particular location or facility. For example, the housing 102 may be approximately 0.25 m (10 inches) in width by approximately 0.23 m (9 inches) in height by approximately 0.23 m (9 inches) in depth, and may weigh approximately 5.5 kg (12 lbs).

Operator controls 106, such as adjustable knobs, buttons, switches, and the like, are provided on the exterior of the housing 102. As described below, the operator controls 106 control aspects of the vitrectomy system 100, such as the cut speed of the vitrector, the level of aspiration, amount of illumination, etc.

In addition, a vitrector connection 108, e.g., a luer connection, is provided on the exterior of the housing 102 to removably couple a vitrector to the components in the housing 102. An air exchange connection 110, e.g., a luer connection, is also provided on the exterior of the housing 102 to removably couple an air exchange tubing set to the components in the housing 102. Additionally, an aspiration cassette 111 is removably received in a cassette receptacle 103 defined by the housing 102 and coupled to the components in the housing 102, e.g., via a luer. As described further below, the aspiration cassette 111 provides aspiration vacuum via an aspiration cassette connection 109 and receives aspirated vitreous gel and saline. Furthermore, a gas source 112 is removably coupled via a gas source connector to the components in the housing 102.

Figure 2:
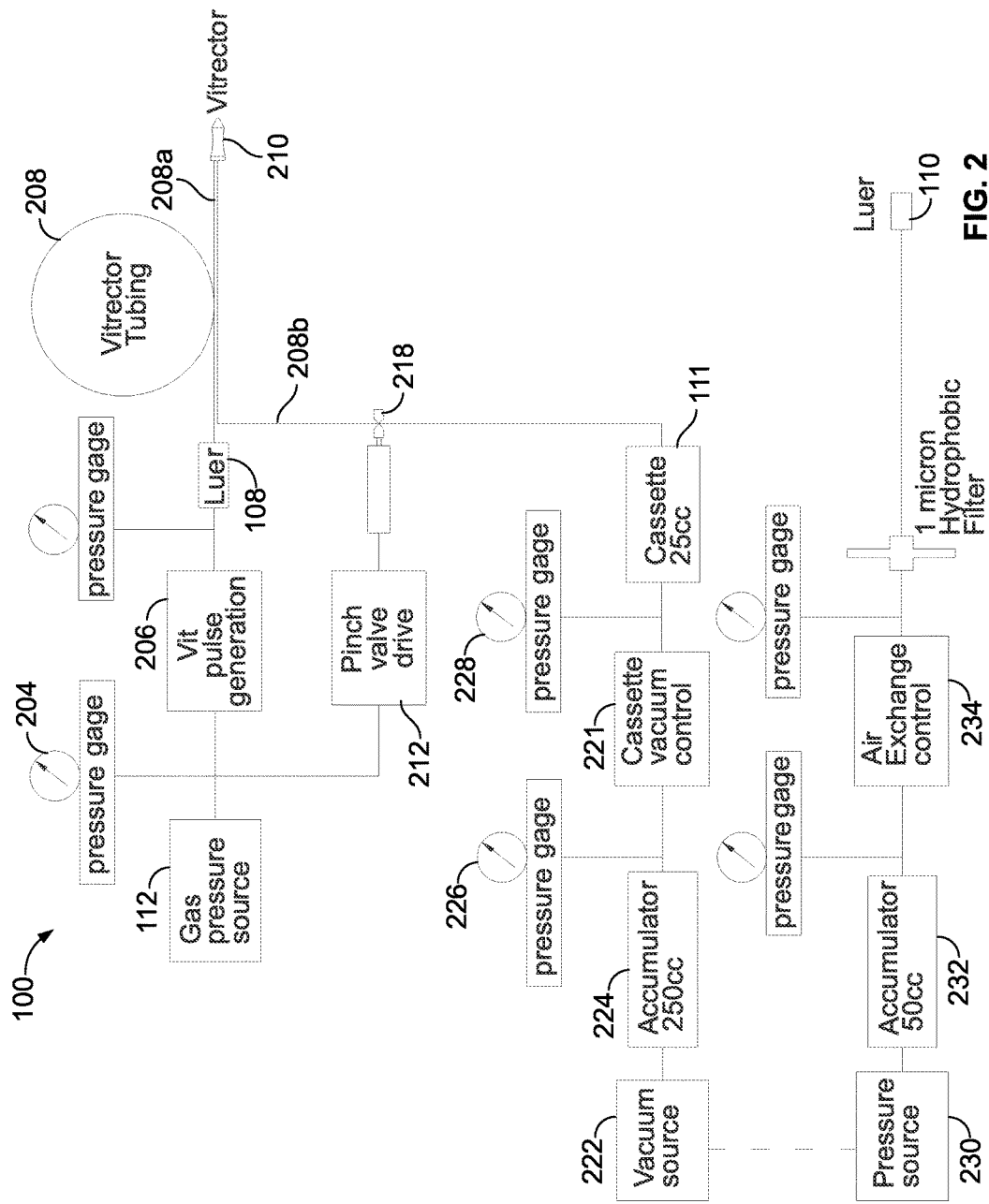
FIG. 2 illustrates pneumatics for an example vitrectomy system according to aspects of the present invention.

Referring to FIG. 2, example pneumatics for the vitrectomy system 100 are illustrated. The vitrectomy system 100 pneumatically drives a low-pressure gas-driven vitrector 210. An operator of the vitrectomy system 100 activates a cut/aspirate mode via the controls 106 to operate the vitrector 210. The gas source 112 provides input gas for driving the vitrector 210. The input gas is regulated at the gas source 112 to a lower input pressure, e.g., approximately 80 psig, which is monitored by a pressure transducer 204.

A pulse-generating system 206 receives the gas from the gas source 112 and generates pulses of gas pressure that drive the vitrector 210. The gas pressure in the pulse-generating system 206 is further regulated to a lower pressure, e.g., approximately 16 psig. The pulses of gas cause a cutting mechanism of the vitrector 210 to open and close according to a cycle. The open/close action of the cutting mechanism cuts the vitreous gel when the vitrector 210 is applied to the eye. The rate at which the pulse-generating system 206 produces the pulses of gas depends on a cut speed the operator selects for the vitrector 210 via the controls 106. In some embodiments, for example, the cut speed may be selected from a range of approximately 60 cuts per minute (cpm) to approximately 2500 cpm.

Vitrector tubing 208 extends between the vitrector connection 108 shown in FIG. 1 and the vitrector 210. The vitrector tubing 208 includes a first tube 208a. The vitrector connection 108 couples the first tube 208a to the pulse-generating system 206 disposed at the housing 102. The first tube 208a carries the pressure pulses from the pulse-generating system 206 to the vitrector 210.

The vitrector tubing 208 also includes a second tube 208b. The aspiration cassette connection 109 couples the second tube 208b to the aspiration cassette 111 disposed in the recess 103. The second tube 208b provides a vacuum to the vitrector 210. The aspiration cassette 111 is removably coupled to a vacuum source 222 and collects aspirant received from the vitrector 210 via the second tube 208b.

The vitrector tubing 208, for example, may include twin-bore PVC tubing having a length of approximately 1 m to approximately 2 m. For a length of approximately 1 m, each tube 208a, b may have an inner diameter of approximately 0.81 mm (0.032 inches) and an outer diameter of approximately 2.4 mm (0.094 inches). For a length of approximately 2 m, each tube 208a, b may have an inner diameter of approximately 1.6 mm (0.062 inches) and an outer diameter of approximately 3.2 mm (0.125 inches). The tubing length is determined in part by the desired distance between a patient and the housing 102. In other words, the tubing length should allow the operator to extend the vitrector 210 to a patient positioned suitably away from the housing 102. In addition, the tubing length should provide sufficient slack so that the operator can manipulate the vitrector 210 in space without significant restriction.

The vitrector tubing 208 may be selected from an array of standard-sized tubing formed from medical grade materials. Specifically, from the array of choices, tubing of varying lengths, inner diameters, outer diameters, and durometers may be evaluated for their performance for various configurations of components, e.g., pneumatic components, for the vitrectomy system 100. The vitrector tubing 108 provides sufficient gas flow to drive the vitrector 210 at the required cut speeds. The highest cut speed requires the highest gas flow in the vitrector tubing 208 leading to the vitrector 210.

The gas source 112 also provides input gas for driving a pinch valve drive 212. The pinch valve drive 212 in turn operates a pinch valve 218 which controls aspiration from the eye during the procedure. An air cylinder of the pinch valve 218 closes the second tube 208*b* of the vitrector tubing 208 to block flow. To allow aspiration through the second tube 208*b*, pressure is applied to the pinch valve 218 which causes the air cylinder to retract. Pressure is applied to the pinch valve 218 when the cut/aspirate mode is activated or when the aspiration cassette 111 is missing. When the cut/aspirate mode is deactivated, the pressure is relieved from the pinch valve 218 causing the pinch valve 218 to pinch and close the second tube 208*b*. When the cut/aspirate mode is deactivated, closure of the pinch valve 218 is delayed to allow the second tube 208*b* to vent to atmosphere. In some embodiments, the pinch valve 218 pinches the second tube 208*b* against a surface of the aspiration cassette 111.

As described previously, the aspiration cassette 111 is coupled to the second tube 208*b* of the vitrector tubing 208 and the vacuum source 222. The vacuum in the aspiration cassette 111 from the vacuum source 222 draws aspirant from the vitrector 210 via the second tube 208*b* to a vial in the aspiration cassette 111. The vacuum level in the aspiration cassette 111 and the level of aspiration are controlled by an adjustable vacuum control 221 provided with the controls 106. When the cut/aspirate mode is deactivated, closure of the pinch valve 218 is delayed also to allow the aspiration cassette 111 to vent to atmosphere. When the pinch valve 218 closes, the vacuum in the aspiration cassette 111 returns to the level determined by the vacuum control 221. The vacuum level of the aspiration cassette 111 is monitored with a pressure transducer 228. In operation, the aspiration cassette 111 may be positioned substantially level with the patient's eye, thereby minimizing aspiration perturbations caused by the fluid column between the aspiration cassette 111 and the eye.

Figure 11:
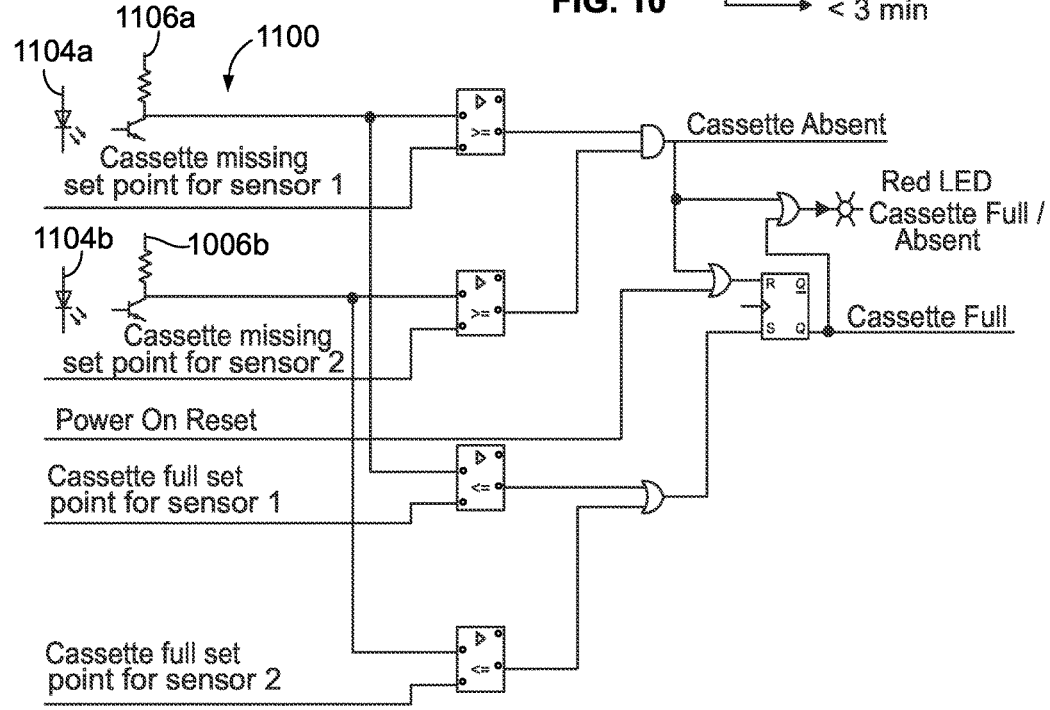
FIG. 11 illustrates an example sensing system for a vial of an aspiration cassette in a vitrectomy system according to aspects of the present invention.

The vial of the aspiration cassette 111, for example, may have a volume of approximately 25 cc. The volume of aspirant received in the vial may be monitored with a sensor system 1100 shown in FIG. 11. In addition to detecting whether a vial contains a threshold volume of aspirant, the sensor system 1100 also detects whether the aspiration cassette 111 is missing from the vitrectomy system 100. The sensor system 1100 includes a pair of infrared light emitting diodes (LED's) 1104*a, b* that are arranged to project two separate infrared beams through the vial. A pair of transistors 1106*a, b* are correspondingly positioned to receive the infrared beams projected through the vial. When the aspiration cassette 111 is missing from the vitrectomy system 100, the infrared beams do not pass through the vial and thus experience substantially no scatter. Because there is substantially no scatter, the infrared energy reaching the transistors 1106*a, b* is substantially equal to the maximum. A CASSETTE MISSING threshold corresponding to this maximum level of infrared energy is set. When both of the transistors 1106*a, b* receive infrared energy that is greater than the CASSETTE MISSING threshold, the aspiration cassette 111 is considered to be missing.

When the aspiration cassette 111 is installed and present in the vitrectomy system 200, the infrared beams experience some scatter due to the vial and the amount of infrared energy reaching the transistors 1106*a, b* is reduced to a level below the CASSETTE MISSING threshold. As the aspirant fills the vial, the LED's 1104*a, b* are positioned so that the infrared beams have to pass through the aspirant when the vial becomes substantially full with aspirant. When the infrared beams pass through the aspirant, the infrared beams experience additional scattering and the infrared energy reaching the transistors 1106*a, b* is reduced further. A CASSETTE FULL threshold corresponding to this reduced level of energy is determined. When either transistor 1106*a, b* receives infrared energy lower than the CASSETTE FULL threshold, the vial is considered to be full. In general, the strength of the signal received by the transistors 1106*a, b* indicates whether aspiration cassette 111 is not present in the vitrectomy system 100 or whether the volume of aspirant has reached a certain volume. After the vitrectomy system 100 detects that the vial is full, the vitrectomy system 100 may be reset when it detects that the aspiration cassette 200 has been removed, or when the vitrectomy system 100 is reset by a POWER/RESET function via the controls 106.

Referring again to FIG. 2, the vitrectomy system 200 generates a vacuum internally via the vacuum source 222. The maximum vacuum, for example, may be approximately 500 mm Hg to approximately 700 mm Hg (at sea level). The vacuum source 222 does not operate if the vitrectomy system 100 is stopped due to a detected error condition, e.g., if there is a problem with the input gas pressure or the battery charge level or if the aspiration cassette 111 is missing.

The vacuum source 222 is coupled to a vacuum accumulator 224. The vacuum accumulator 224 stores system vacuum and has the capacity to maintain vacuum in the aspiration cassette 111 even when the vacuum source 222 is not operating. The accumulator, for example, may have a volume of approximately 250 cc. The vacuum accumulator 224 also smoothes variations when the vacuum source 222 is operating. The vacuum level in the vacuum accumulator 224 is monitored with a pressure transducer 226.

The vitrectomy system 100 generates low pressure air internally via a pressure source 230 to provide air exchange. The air exchange controls infusion pressure of an infusion fluid by adjusting a pressure in an irrigation bottle during the procedure. The air exchange may also deliver low pressure air to the eye during an air-fluid exchange. The low pressure air is directed to an accumulator 232. The accumulator 232 stores pressure, e.g., at approximately 5 psig. The accumulator 232 also smoothes variations when the pressure source 230 is operating. Once the low pressure source 230 provides the required pressure in the accumulator 232, the accumulator 232 has the capacity to allow the pressure source 230 to be implemented as a supplemental vacuum source. The output pressure from the pressure source 230 is determined by an air exchange control 234 provided with the controls 106. The air exchange may be maintained regardless of whether the cut/aspirate mode is activated or deactivated or whether there are error conditions. Advantageously, the internal generation of low pressure air allows the vitrectomy system 100 to operate independently of any special external air pressure source.

In one embodiment, an irrigation fluid bottle containing saline is connected to the air exchange connection 110 via an air exchange tube set. The air exchange tube set is a PVC tubing set intended to deliver forced air or fluid during ophthalmic surgery. The air exchange tube set includes a three channel IV spike for insertion into the bottle. The three-way spike is designed to deliver air from the pressure source 230 through the saline, while the dual PVC tubing administers air and saline. The dual PVC tubing has a three-way stopcock for proper connection. The irrigation fluid bottle may be positioned so that it is substantially level with the eye. The spike from the air exchange tube set is coupled to the bottle and an infusion cannula is coupled to the other end of the air exchange tube set. The air exchange control 234 is set to provide a desired infusion pressure.

FIGS. 3A-B, 4, and 5 illustrate examples of how the vitrectomy system 100 may drive the vitrector 210 and control the pinch valve 218. The gas pressure source 112, for instance, includes a conventional tank 312a containing carbon dioxide ($CO_2$) at a pressure of approximately 900 psig. The gas tank 312a is removably received by the housing 102 and screwed to a gas source connector until it is firmly seated.

Employing a conventional tank to supply gas to the vitrectomy system 100 allows the vitrectomy system 100 to be operated without access to a special gas supply system typically available in special hospital facilities. The vitrectomy system 100, for example, may accept gas cylinders ranging in size from 12 g to 33 g. The size of such gas cylinders enhances the portability of the vitrectomy system 100. Moreover, compatibility with standard smaller off-the-shelf gas tanks enhances the convenience and cost effectiveness of using the vitrectomy system 100. Additionally, the smaller size and relatively lower cost of the gas cylinder allows it to be included in a convenient disposable package that is used for each procedure.

The pressure in the gas tank 312a is regulated, e.g., to a pressure of approximately 80 psig, using a tank-mounted high pressure regulator 312b. Protection from liquid $CO_2$ intrusion into the high pressure regulator 312b is provided by an adapter between the gas source connector and the high pressure regulator 312b. The pressure transducer 204 is used to monitor the output from the high pressure regulator 312b. If the pressure drops below a minimum threshold, e.g., 70 psig, the vitrectomy system 100 shuts off.

The low pressure regulator 313 reduces the gas pressure, e.g., to approximately 16 psig. The pulse-generating system 206 includes a valve combination 314. The gas from the low pressure regulator 313 is directed to the valve combination 314 to generate pressure pulses for driving the vitrector 210. The pressure pulses cause the pressure at the vitrector 210 to vary according to a cycle, and the varying pressure at the vitrector 210 causes the cutting mechanism of the vitrector 210 to open and close.

Figure 3A:
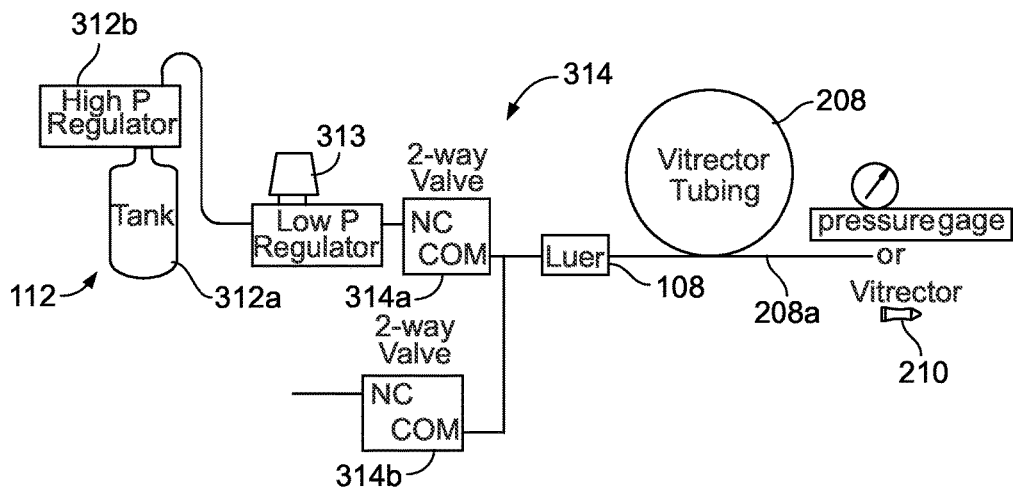
FIG. 3A illustrates an example of how a vitrectomy system may drive a vitrector according to aspects of the present invention.
Figure 4:
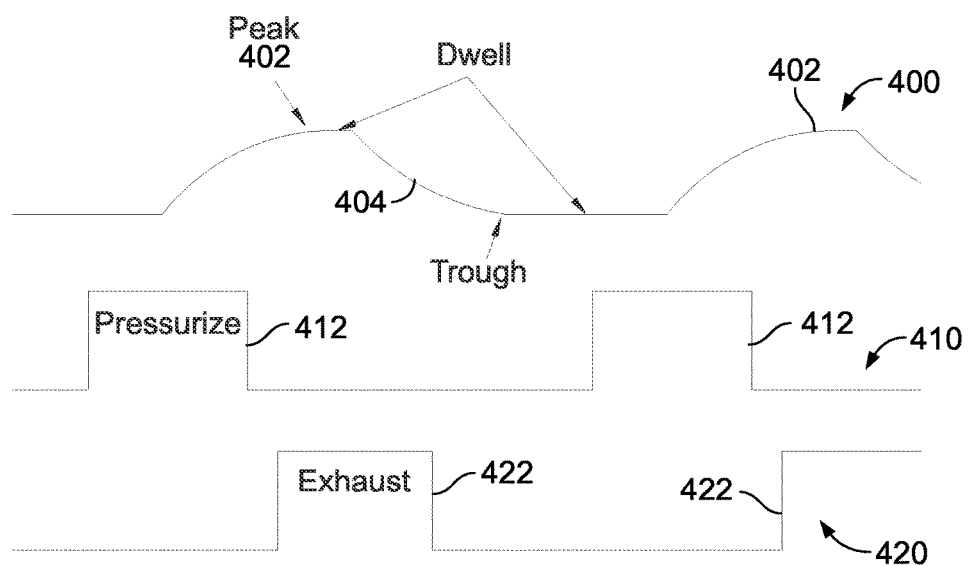
FIG. 4 illustrates aspects of a cut cycle corresponding to the example of FIG. 3A.

As shown in the example embodiment of FIG. 3A, the valve combination 314 may include a two-way pressurize valve 314a and a two-way exhaust valve 314b. The pressurize valve 314a is coupled to the low pressure regulator 313 and to the vitrector 210. At the beginning of a cut cycle, the pressurize valve 314a opens for approximately 6 ms to raise the pressure to a maximum of approximately 14 psig at the vitrector 210. A pressure curve 400 shown in FIG. 4 illustrates the pressure at the vitrector 210 during the cut cycle as a function of time. A corresponding curve 410 shown in FIG. 4 indicates when the pressurize valve 314a remains open during a period 412 in the cut cycle. The maximum pressure is shown as peak 402.

The exhaust valve 314b is coupled to the vitrector 210 and to atmosphere through a muffler. During the cut cycle, the exhaust valve 314b opens for approximately 18 ms to reduce the pressure at the vitrector 210 from the maximum pressure to a minimum pressure of approximately 4 psig. A curve 420 shown in FIG. 4 indicates when the exhaust valve 314b remains open during a period 422 in the cut cycle. Taken together the curves 400, 410, and 420 illustrate how the pressure at the vitrector 210 responds to the opening/closing of the pressurize valve 314a and the opening/closing of the exhaust valve 314b. The minimum pressure is shown in pressure curve 400 of FIG. 4 as trough 404. As illustrated in FIG. 4, the opening and closing of the valves 314a, b are timed to achieve a desired pressure profile, e.g., the pressure curve 400. With certain types of valves, the time and manner in which the valves 314a, b open may be different from the time and manner in which the valves 314a, b close. Thus, to account for this asymmetric behavior in FIG. 4, for example, there is a delay of approximately 8 ms between the time when the pressurize valve 314a is closed and the time when the exhaust valve 314b is opened.

Figure 3B:
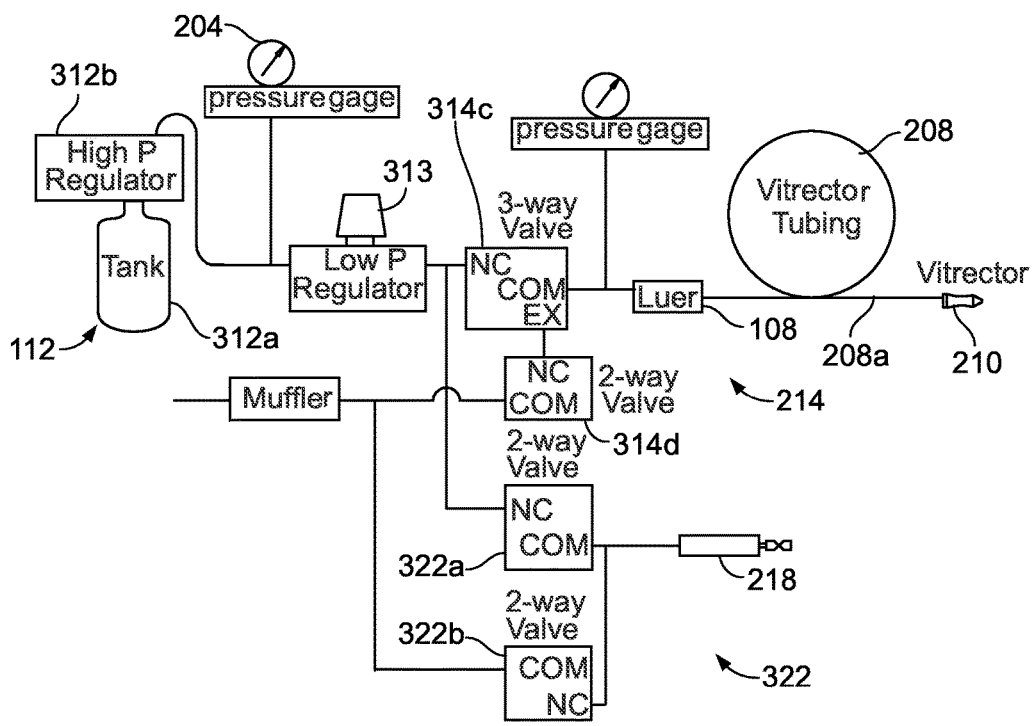
FIG. 3B illustrates another example of how a vitrectomy system may drive a vitrector according to aspects of the present invention.

Alternatively, as shown in the embodiment of FIG. 3B, the valve combination 314 includes a three-way pressurize valve 314c and a two-way exhaust valve 314d. The pressurize valve 314c is coupled to the low pressure regulator 313, the vitrector 210, and the exhaust valve 314d. The two-way valve 314d is coupled to the pressurize valve 314c and to atmosphere through a muffler. At the beginning of the cut cycle, the pressurize valve 314a opens for approximately 6 ms to raise the pressure to a maximum of approximately 14 psig at the vitrector 210. When the pressurize valve 314c closes, the vitrector 210 is coupled to the exhaust valve 314d via the pressurize valve 314c. Thus, the exhaust valve 314d opens at the same time that the pressurize valve 314c closes. The exhaust valve 314d couples the vitrector 210 to atmosphere via a muffler. The exhaust valve 314d remains open for approximately 18 ms and reduces the pressure at the vitrector 210 from the maximum to a minimum of approximately 4 psig.

In general, the embodiments of the pulse-generating system 206 shown in FIGS. 3A-B include a first valve and a second valve, where the first valve and the second valve are operable to raise and reduce the pressure at the vitrector 210 according to a cycle that drives the vitrector 210. At a first time in the cycle, the pulse-generating system 206 raises the pressure at the vitrector 210 to a maximum pressure. At a second time in the cycle, the pulse-generating system 206 reduces the pressure at the vitrector 210 to a minimum pressure that is greater than ambient. Instead of exhausting the gas from the vitrector 210 and in the vitrector tubing 208 until the pressure reaches ambient, the pressure at the vitrector 210 and in the vitrector tubing 208 is maintained at a minimum pressure that is greater than ambient. As a result, to raise the pressure to the maximum pressure during the cut cycle, the gas source 112 is required to supply less gas than would otherwise be required if the pressure at the vitrector 210 and in the vitrector tubing 108 were permitted to drop to ambient. Accordingly, the embodiments use gas more efficiently during the cut cycle and deplete the supply gas from the gas source 112 more slowly.

The efficient use of gas by the vitrectomy system 100 is particularly advantageous if the vitrectomy system is employed with gas tanks that are 12 g to 33 g in size, for example. The embodiments shown in 3A-B can provide approximately 6 minutes to approximately 19 minutes of vitrector operation when gas pressure in the system is kept at or above a minimum threshold greater than ambient. The operating time depends on the cut speed of the vitrector 210. For example, a 16 g cylinder tank may provide approximately 8 to approximately 9 minutes of vitrector operation when the vitrector 210 is operated at 1200 cpm. Of course, in some embodiments, an adapter is available to allow the vitrectomy system 100 to be used with a special gas supply system, if available. The special gas supply system effectively extends the operating time of the vitrectomy system 100 indefinitely.

Although the embodiments described previously raise the pressure to a maximum of approximately 14 psig at the vitrector 210 and reduce the pressure to a minimum pressure of approximately 4 psig, the maximum and minimum pressures during the cut cycle may be different in other embodiments. The maximum and minimum pressures are selected according to the pressures required to operate the vitrector 210. For instance, the maximum pressure during the cut cycle should be sufficient to cause the cutting mechanism of the vitrector 210 to close completely and to achieve the required cut speed. Higher cutting speeds can be achieved with greater spring force in the cutting mechanism of the vitrector 210 and correspondingly higher applied pressure. To promote efficient use of gas, the maximum pressure is preferably the lowest pressure required for the cutting mechanism to close completely. The pressure required for the cutting mechanism to close completely depends partially on the force required to overcome the friction as well as the spring force associated with the cutting mechanism of the vitrector 210.

Meanwhile, the minimum pressure during the cut cycle should be sufficiently low to cause the cutting mechanism to open completely. To promote efficient use of gas further, the minimum pressure is preferably the highest possible pressure that still ensures that the cutting mechanism of the vitrector 210 opens completely. In general, embodiments employing the valve combination 314 described above achieve more efficient use of gas by minimizing the difference between the maximum and minimum pressures during the cut cycle. In some embodiments, the greatest efficiencies are achieved with a pressure difference of approximately 8 psig to approximately 10 psig.

The pressurize valve and the exhaust valve are opened for the necessary periods of time to achieve a maximum pressure and a minimum pressure, respectively. The periods of time, as well as the minimum and maximum pressures, depend on the structure and configuration of the valve combination 314 and the vitrector 210. Typically, the pressurize valve does not remain open longer than half the time for the cut cycle, because it takes more time for the exhaust valve to reduce the pressure to the minimum than it takes for the pressurize valve to raise the pressure to the maximum. To optimize air flow in the vitrectomy system 100, the pulse-generating system 206 may be adjusted to deliver a maximum pressure that is sufficient to provide the largest cut speed during the shortest amount of time required to open the pressurize valve.

In addition to achieving more efficient use of gas and extending the operating time provided by the gas source 112, it has been discovered that embodiments that minimize the difference between the maximum and minimum pressures during the cut cycle also provide additional advantages. In particular, the embodiments reduce the noise associated with operating the vitrectomy system 100. Noise is a distraction during the procedure. Conventionally, mufflers are used in vitrectomy systems to reduce noise, but the noise is generally difficult to muffle due to the pulsing nature of the vitrectomy system 100. Changing the minimum and maximum pressures as described above, however, yields greater noise reduction, because less air is being moved during each cut cycle.

Furthermore, the embodiments also reduce the amount of stiffness that the gas pressure causes in the vitrector tubing 208. The stiffness increases with greater average operation pressure in the vitrector tubing 208. The vitrector 210, however, is easier to manipulate when the vitrector tubing 208 remains more flexible.

In addition, when the difference between the maximum and minimum pressures is larger and the vitrector tubing 208 is stiffer, the vitrector tubing 208 has a greater tendency to bounce or vibrate and transfer disturbances to the operator's hand holding the vitrector 210. Accordingly, reducing the stiffness of the vitrector tubing 208 gives operators a greater tactile feel and steadier control of the vitrector 210.

As discussed previously, the vitrector tubing 108 must provide sufficient gas flow to drive the vitrector 210 at the required cut speeds. The vitrectomy system 100, however, also minimizes consumption of the gas from the gas source 112. A longer tube with larger inner diameter provides a higher gas flow rate and results in more gas consumption. Conversely, a shorter tube with smaller inner diameter provides a lower gas flow rate and results in less gas consumption. As discussed previously, the length of the vitrector tubing 208 is determined by practical considerations. For example, the length of the vitrector tubing 208 is not shorter than 1 meter. Thus, for a given length of the vitrector tubing 208, the inner diameter may be reduced to the point where the gas flow cannot drive the vitrector 210 at the required cut speeds. In addition to minimizing gas consumption, the smaller inner diameter results in less stiffness in the vitrector tubing 210.

Referring again to FIG. 3B, the pinch valve drive 212 also employs a valve combination 322 to control the pressure that drives the pinch valve 218. The valve combination 322 includes a pressurize valve 322a and an exhaust valve 322b. The pressurize valve 322a is connected to the low pressure regulator 313 and an air cylinder for the pinch valve 218. The air cylinder of the pinch valve 218 may be a reverse acting (spring extended) air cylinder that aids in closing the second (aspiration) tube 208b of the vitrector tubing 208. In operation, the pressurize valve 322a opens, e.g., for approximately 100 ms, to open the pinch valve 218. The exhaust valve 322b is connected to the air cylinder of the pinch valve 218 and to atmosphere through a muffler. The exhaust valve 322b opens, e.g., for approximately 100 ms, to close the pinch valve 218.

Figure 5:
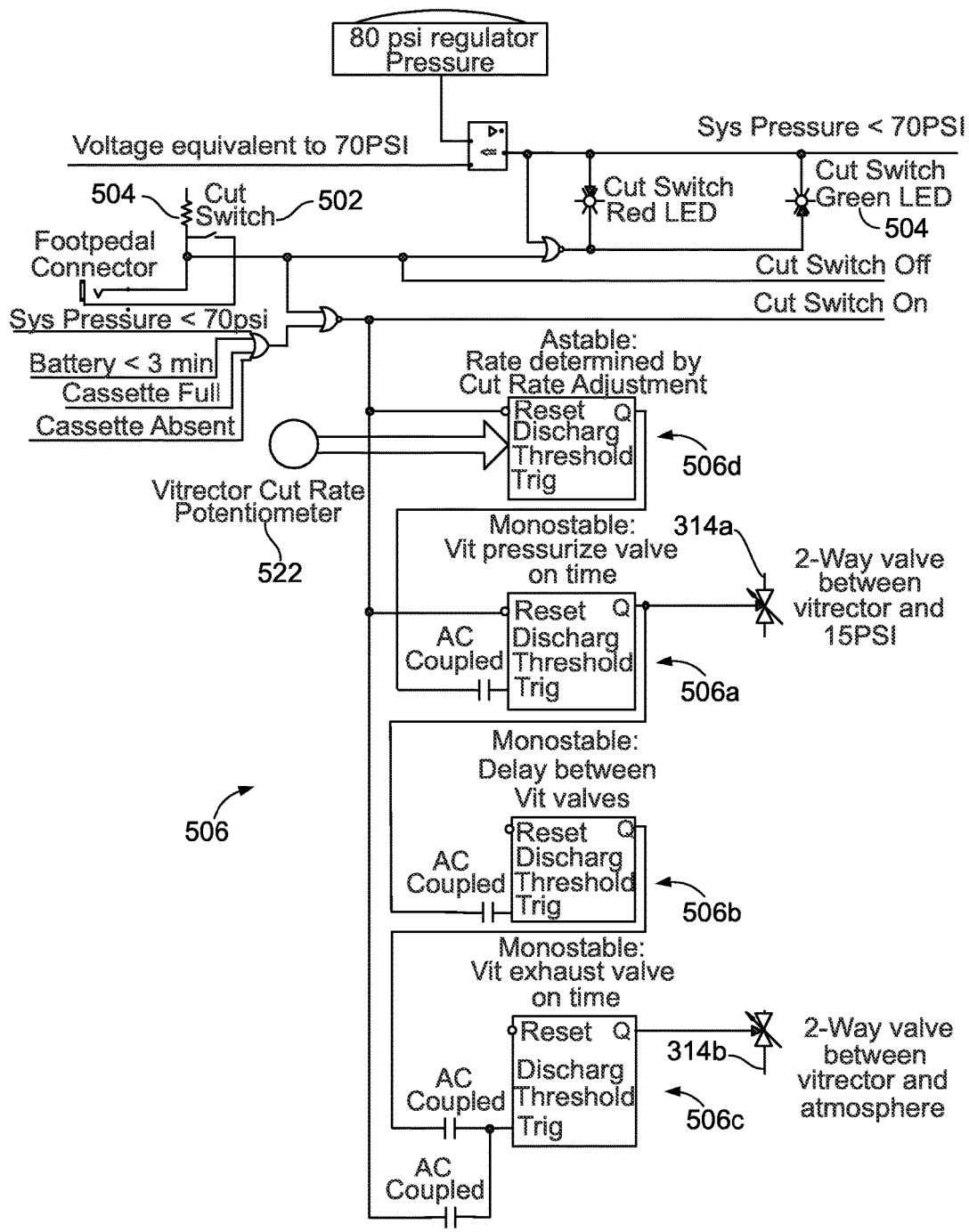
FIG. 5 illustrates example electronics corresponding to the example of FIG. 3A.

FIG. 5 illustrates example electronics for driving the vitrector 210 and controlling the pinch valve 218 for a vitrectomy system 100 that employs the valve combination 314 shown in FIG. 3A. The vitrector 210 is controlled by an illuminated toggle switch 502 and an adjustable potentiometer 522 provided with the controls 106. The adjustable potentiometer 522 determines the cut rate for the vitrector 210. The switch 502 is operated to alternate between activating and deactivating the cut/aspirate mode and to respectively enable or disable cutting with the vitrector 210. When the cut/aspirate mode is deactivated, the aspiration system is also returned to atmosphere with the pinch valve 218 closed. The switch 502 is illuminated with a combination RED/GREEN LED 504. The LED is illuminated RED when the available gas pressure falls below a minimum threshold, e.g., approximately 70 psig. The LED is illuminated GREEN when the cut/aspirate mode is activated. The LED is not illuminated when the cut/aspirate mode is deactivated.

Operation of the vitrectomy system 100 is enabled when the switch 502 is switched to activate the cut/aspirate mode. Although embodiments of the vitrectomy system 100 may employ a microprocessor, the embodiment shown in FIG. 5 employs discrete integrated circuit (IC) functional blocks (logic gates, flip-flops, multivibrators, etc.). In particular, the vitrectomy system 100 employs a multivibrator chain 506 that determines operation of the vitrector 210 according to the cut cycle. Thus, when the switch 502 is switched to ON, the switch pull-up resistor 504 is grounded and the RESET signal is removed from the multivibrator chain 506. The monostable multivibrator 506a is triggered to open the two-way pressurize valve 314a. Triggering the monostable multivibrator 506a causes the pressure to increase at the vitrector 210 and the cutting mechanism to close. After the pressurize valve 314a is closed for the required amount of time, e.g., approximately 6 ms, the next monostable multivibrator 506b is triggered. As described previously, there is a delay, e.g., approximately 8 ms, between the time when the pressurize valve 314a is closed and the time when the exhaust valve 314b is opened. After the delay time expires, the final monostable multivibrator 506c in the chain 506 is triggered. The monostable multivibrator 506c opens the two-way exhaust valve 314b and causes the cutting mechanism of the vitrector 210 to open. The exhaust valve 314b closes after the required amount of time, e.g., approximately 18 ms. When the cut/aspirate mode is activated with the switch 502, an astable multivibrator 506d runs at the cut rate selected for the vitrector 210. The astable multivibrator 506d triggers the monostable multivibrator 506a controlling the pressurize valve 314a and repeats the cut cycle.

During the procedure, the tip of the vitrector 210 is placed at an area of vitreous gel requiring removal. The cut/aspirate mode may be activated through the toggle switch 502 or a foot pedal. When the cut/aspirate mode is activated, the vitrectomy system 100 cuts and aspirates at the levels determined by the adjustable cut rate control 522 and the adjustable vacuum control 221. Once the desired volume of vitreous gel has been removed, the cut/aspirate mode is deactivated by pressing the toggle switch 502 again or by releasing the foot pedal.

When the cut/aspirate mode is deactivated, the cutting mechanism of the vitrector 210 stops immediately. In addition, the monostable multivibrator 506c controlling the exhaust valve 314b is triggered to force the cutting mechanism of the vitrector 210 to open.

Figure 6:
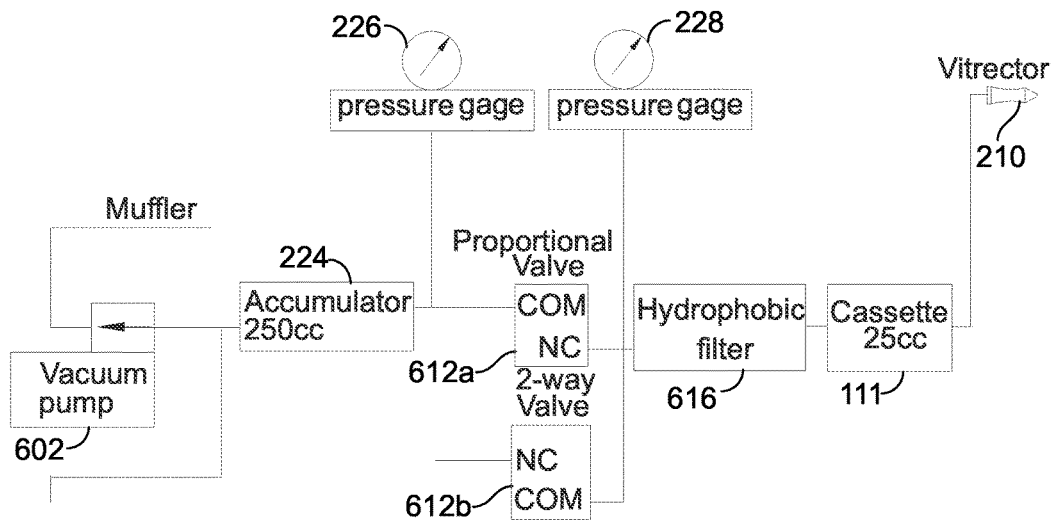
FIG. 6 illustrates an example of how a vitrectomy system may control aspiration according to aspects of the present invention.
Figure 7:
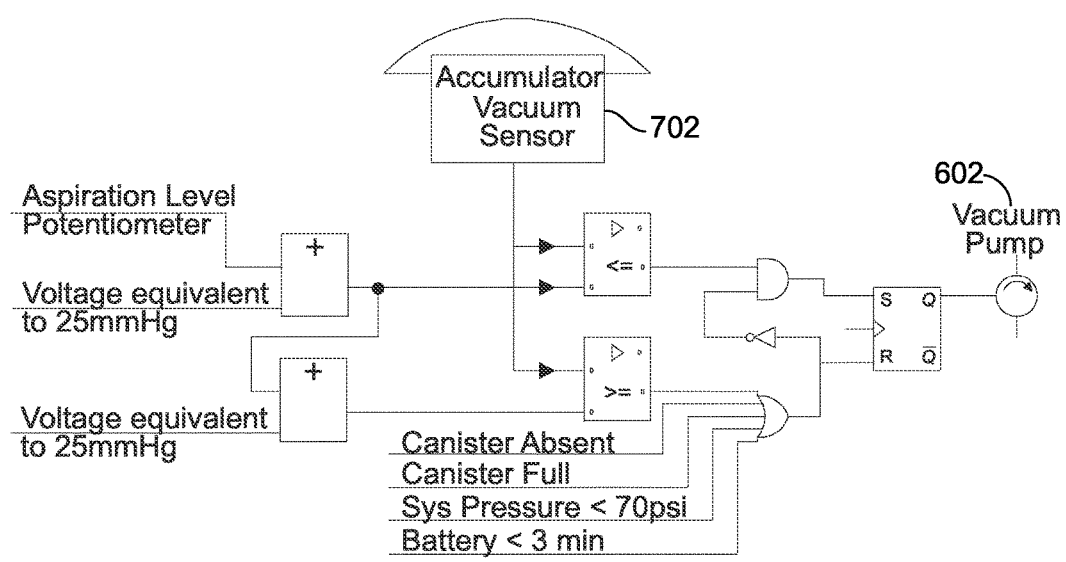
FIG. 7 illustrates example electronics corresponding to the example of FIG. 6.

FIG. 6 illustrates an example of how the vitrectomy system 100 may control aspiration. The vacuum source 222 includes a vacuum pump 602, such as a 6 VDC diaphragm pump. The exhaust for the vacuum pump 602 is connected to a muffler. The vacuum pump 602 is activated when the vacuum at the vacuum accumulator 224 drops below a vacuum pressure activation threshold. The vacuum pressure activation threshold, for example, is set to a pressure approximately 25 mmHg above the aspiration level specified by the adjustable vacuum control 221. The vacuum level in the vacuum accumulator 224 is monitored with a pressure transducer 226. As shown in the electronics of FIG. 7, a vacuum level determined by a sensor 702 is compared to the vacuum pressure activation threshold. The vacuum level determined by the sensor 702 is also compared to a vacuum pressure deactivation threshold. The vacuum pump 702 is stopped when the vacuum in the accumulator meets the vacuum pressure deactivation threshold (or when an error condition occurs).

As illustrated further in FIG. 6, a proportional valve 612a and a two-way valve 612b control the vacuum level in the aspiration cassette 111. The proportional valve 612a is coupled to the vacuum accumulator 224 and the aspiration cassette 111 (through a hydrophobic filter 616). The proportional valve 612 is operated to lower the pressure in the aspiration cassette 111 to the value determined by the vacuum control 221. The proportional valve 612a is opened by an amount that minimizes overshoot and vacuum response time. The vacuum level of the aspiration cassette 620 is monitored with a pressure transducer 228. The two-way valve 612b is coupled to the aspiration cassette 111 and to atmosphere. The two-way valve 612b is operated to raise the pressure in the aspiration cassette 111.

Figure 8:
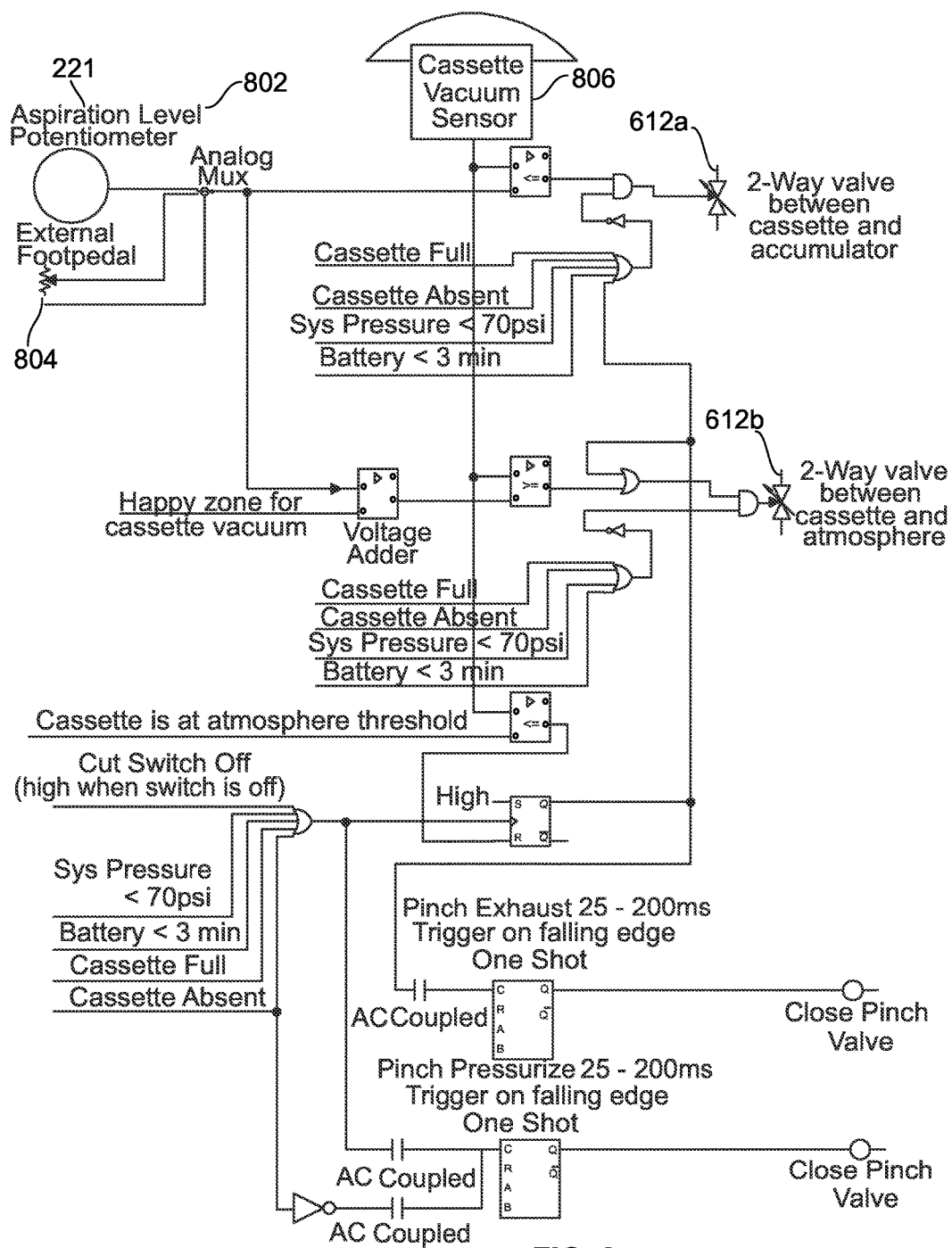
FIG. 8 illustrates additional example electronics corresponding to the example of FIG. 6.

FIG. 8 illustrates example electronics for controlling the aspiration in the vitrectomy system 100. The operator controls the aspiration level by the adjustable vacuum control 221, which includes a potentiometer 802 or a linear foot pedal 804. The adjustment allows the vacuum to be set, for example, from approximately 25 mmHg to approximately 500 mmHg. The setting is compared with a vacuum sensor 806 that is coupled to the aspiration cassette 111. The vacuum sensor 806 may be similar to the sensor 702 that monitors the vacuum of the vacuum accumulator 224. In both cases, the sensors have a 4 VDC range which equates to 15 psig (approximately 775.7 mmHg).

If the vacuum level in the aspiration cassette 111 is less than the aspiration level set by the operator (and there is no error condition or cassette venting in progress), the two-way valve 612a opens and couples the aspiration cassette 111 to the vacuum accumulator 224. The aspiration cassette 111 passes air to the vacuum accumulator 224 causing a reduction of pressure in the aspiration cassette 111. Once the vacuum level in the aspiration cassette 111 matches the aspiration level set by the user, the two-way valve 612a closes and decouples the aspiration cassette 111 from the vacuum accumulator 224.

The aspiration cassette 111 is coupled to atmosphere when the vacuum level in the aspiration cassette 111 is higher than an aspiration cassette vacuum threshold. If the vacuum level in the aspiration cassette 111 is greater than the aspiration cassette vacuum threshold or venting of the aspiration cassette 111 is in progress, the two-way valve 612b allows the aspiration cassette 111 to attain atmospheric pressure.

A second mechanism controls venting of the aspiration cassette 111 to atmosphere when the cut/aspirate mode is deactivated or an alarm condition occurs. In this case, a D latch causes the proportional valve 612a to close the connection between the aspiration cassette 111 and the vacuum accumulator 224, while the two-way valve 612b connects the aspiration cassette 111 to atmosphere. Once the aspiration cassette 111 meets the CASSETTE AT ATMOSPHERE threshold, the D latch is reset and the pinch valve 218 pinches the tube 208b closed. Resetting of the D latch also allows the proportional valve 612a to couple the aspiration cassette 111 to the vacuum accumulator 224 so that the aspiration cassette 111 can be driven subsequently to the vacuum level set by the operator.

The pinch valve 218 is opened for normal aspiration when the cut/aspirate mode is activated (and no error conditions are present). The pinch valve 218 is also opened if the aspiration cassette 111 is removed from the vitrectomy system 100 to install a replacement cassette.

Figure 9:
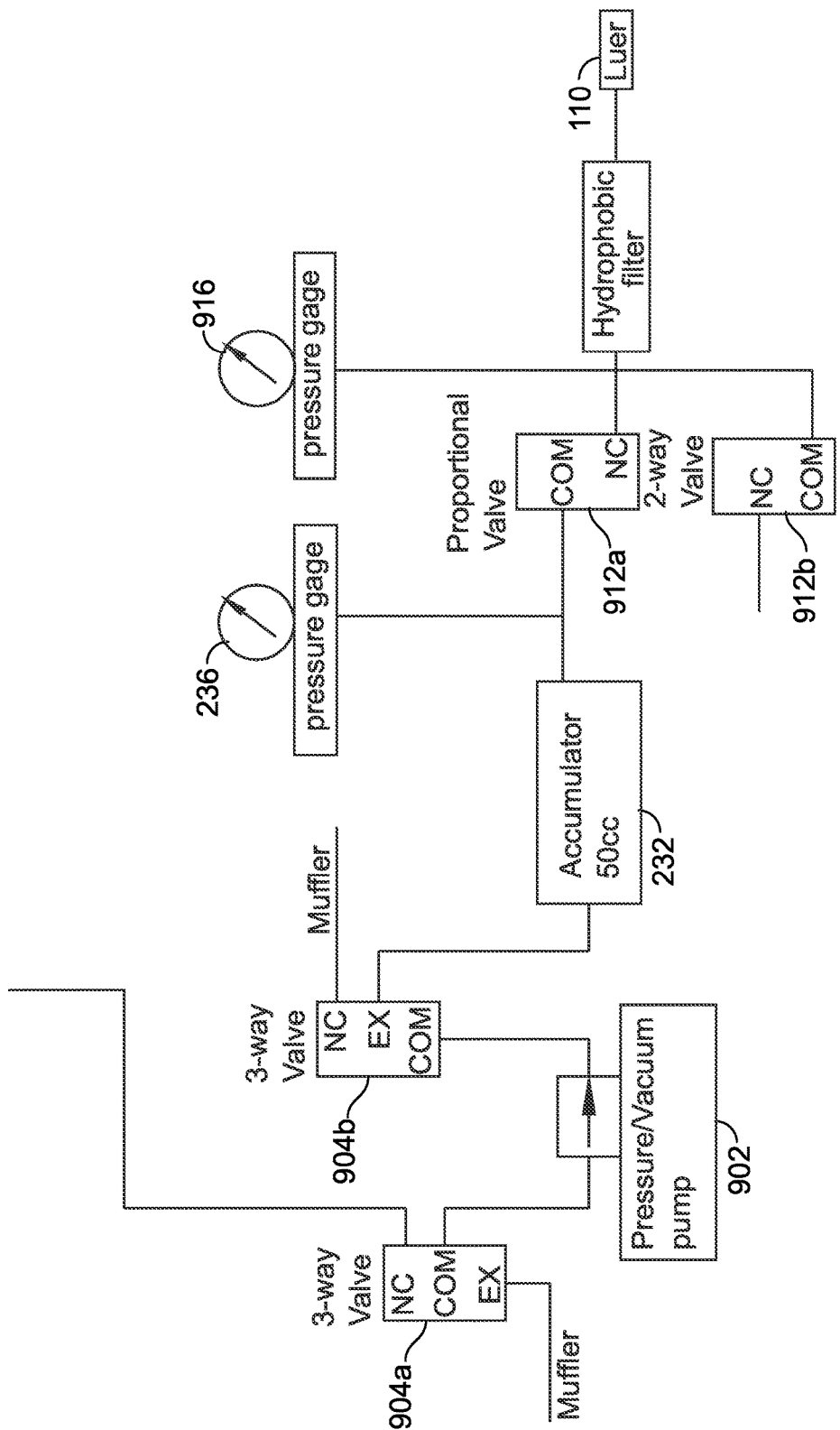
FIG. 9 illustrates an example of how a vitrectomy system may control the air exchange according to aspects of the present invention.

FIG. 9 illustrates an example of how the vitrectomy system 100 may handle air exchange. The pressure source 230 includes a pressure/vacuum pump 902, such as a 6 VDC diaphragm pump. Through two three-way valves 904a, b, the pressure/vacuum pump 902 can be employed for air exchange function as well as aspiration function. The three-way valves 904a, b are configured so that when they are closed, the pressure/vacuum pump 902 delivers pressure for air exchange function. Conversely, when the three-way valves 904a, b are open, the pressure/vacuum pump 902 delivers vacuum for aspiration function. Priority is given to the air exchange function. The pressure/vacuum pump 902 is operated to increase the pressure at the accumulator 232 when the pressure drops below a threshold, e.g., approximately 5 psig. The pressure at the accumulator 232 is monitored with the pressure transducer 236.

As FIG. 9 illustrates further, a proportional valve 912a and a two-way valve 912b are employed to control the output level of the air exchange pressure. The proportional valve 912a is coupled to the accumulator 232 and the output 110 (through a hydrophobic filter). The proportional valve 912a is operated to raise the output pressure to the value set by the air exchange control 234. Once the output pressure reaches the set value, the proportional valve 912a is closed or its opening is adjusted to match a constant flow load. The amount that the proportional valve 912a opens is controlled to minimize overshoot and pressure response time. The output pressure level is monitored by a pressure transducer 916. Meanwhile, the two-way valve 912b is coupled to the output 914 and to atmosphere and is operated to lower the output pressure.

Figure 10:
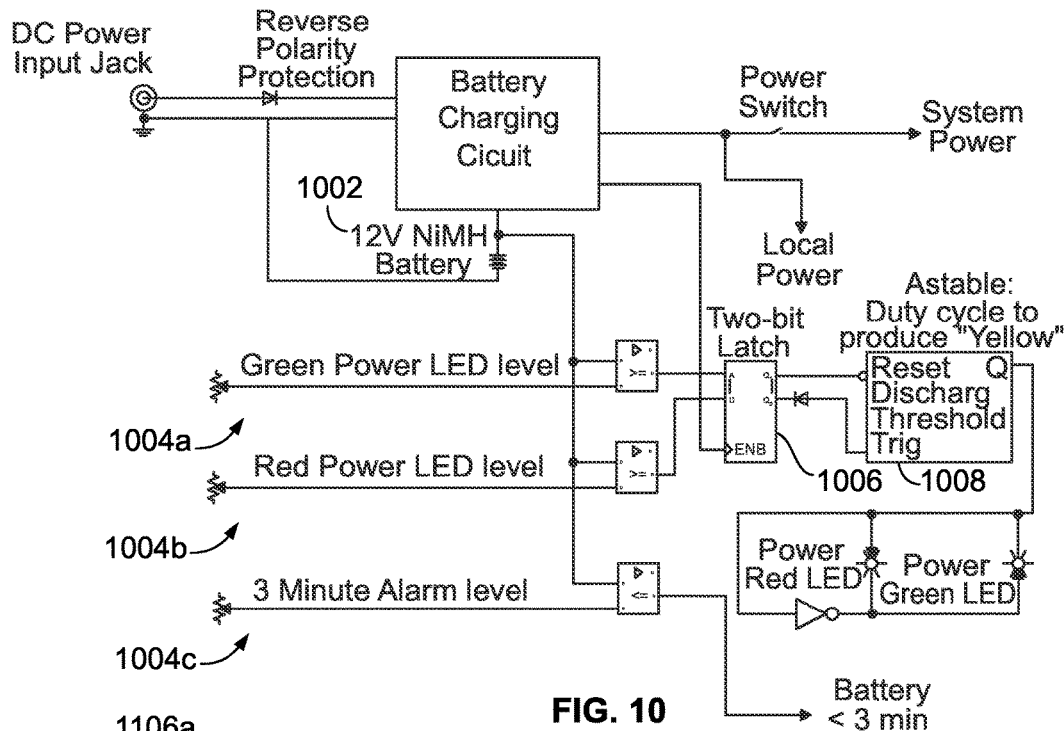
FIG. 10 illustrates an example power supply for a vitrectomy system according to aspects of the present invention.

Referring to FIG. 10, the vitrectomy system 100 employs a rechargeable battery 1002. The vitrectomy system 100 can be coupled to an external power source to recharge the rechargeable battery 1002. It is not necessary, however, for the vitrectomy system 100 to be completely charged to use it. When connected to the external power source, the vitrectomy system 100 operates with the power from the external power source while the rechargeable battery 1002 is recharged. Advantageously, the rechargeable battery 1002 allows the vitrectomy system 100 to be operated without access to an external power source. The rechargeable battery 1002 enhances the portability of the vitrectomy system 100. Moreover, the rechargeable battery 1002 can be conveniently recharged by connecting the vitrectomy system to a conventional electrical wall socket.

It is also not necessary to turn on the vitrectomy system 100 for the battery 1002 to charge. If the vitrectomy system 100, however, is turned on, a power indicator shows the state of battery charge. The power indicator illuminate via a GREEN and a RED LED. If the power indicator illuminates RED, there may not be enough charge to complete the procedure. In some cases, the power indicator may not illuminate due to a depleted battery 1002. Three comparators 1004a-c are utilized to provide a visual indication of the battery run time. The first comparator 1004a determines whether the estimated battery run time exceeds 30 minutes. The second comparator 1004b determines whether the estimated battery run time exceeds 20 minutes. These two comparator outputs pass through a transparent latch 1006 that is enabled when the vitrectomy system 100 is operating from the rechargeable battery 1002, and is selectively enabled during certain periods as the rechargeable battery 1002 is charging. The outputs from the latch 1006 are coupled to an astable multivibrator 1008 that is forced into reset when the battery voltage exceeds 30 minutes (GREEN power indicator) and is forced into trigger when the battery voltage falls below 20 minutes (RED power indicator). Between 20 minutes and 30 minutes, the multivibrator 1008 is allowed to run at a 60 Hz rate (combining RED and GREEN to provide a YELLOW power indicator). The third comparator 1004c determines whether the estimated battery run time is less than 3 minutes, in which case an alarm is provided to alert the operator.

While some components of the vitrectomy system 100 may be reusable, other components, such as the gas cylinder tank 202a, the vitrector 210, the vitrector tubing 208, the aspiration cassette 111, irrigation tubing, etc., may be disposable and provided for use in a single procedure. The disposable components may be conveniently packaged in a single disposable pack, e.g., with Tyvek® material. The vitrector 210, the vitrector tubing 208, the aspiration cassette 111, and the irrigation tubing are disposed in a manner consistent with other contaminated waste.

The vitrectomy system 100 may also include a disposable endoilluminator. The illumination level may be adjusted to a desired amount with the controls 106. The light output is reduced when a probe of the endoilluminator is not in the eye to reduce the possibility of damage to the fibers of the endoilluminator and to increase battery life.

Figure 12A:
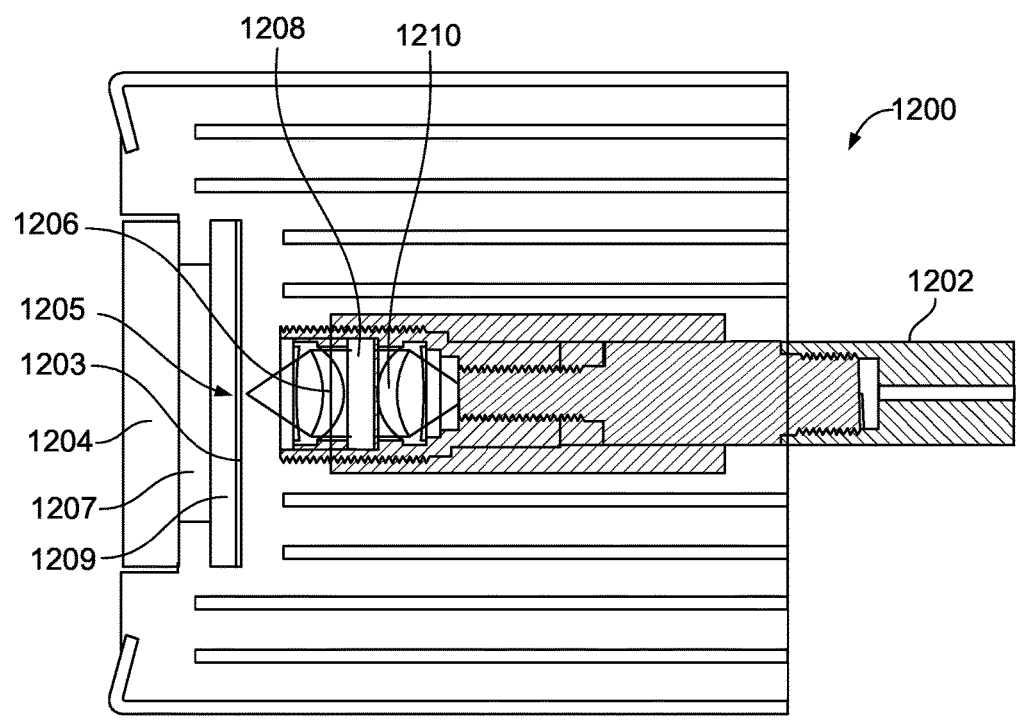
FIG. 12A illustrates an example illumination system in a vitrectomy system according to aspects of the present invention.
Figure 12B:
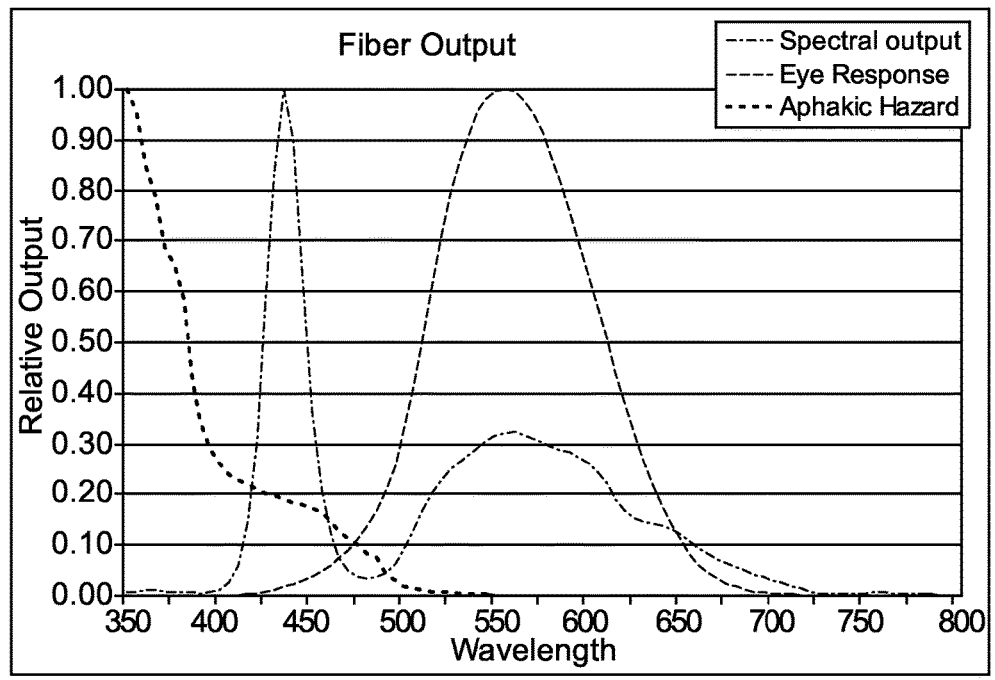
FIG. 12B illustrates the relative spectral output of an LED in the example illumination system of FIG. 12A.

FIG. 12A illustrates an example illumination system 1200 for providing light to the endoilluminator via an output connector receptacle 1202. The output connector receptacle accepts an optical fiber connector. In one embodiment, for example, the optical fiber connector may be constructed from a 19-gauge hypodermic needle (approximately 1.1 mm (0.42 inches) in diameter) having a length of approximately 6.35 cm (2.5 inches). The light source in the illumination system 1200 includes an LED 1205. As shown in FIG. 12A, the LED 1205 is provided on a printed circuit board (PCB) 1203. For example, the LED 1205 may be a blue-violet LED (approximately 435 nm) with a phosphor coating to convert a portion of the light to broadband light of longer wavelength that appears white. The light emitting portion of the LED 1205 may be approximately 2 $mm^2$. FIG. 12B illustrates the relative spectral output of the LED 1205.

Figure 12C:
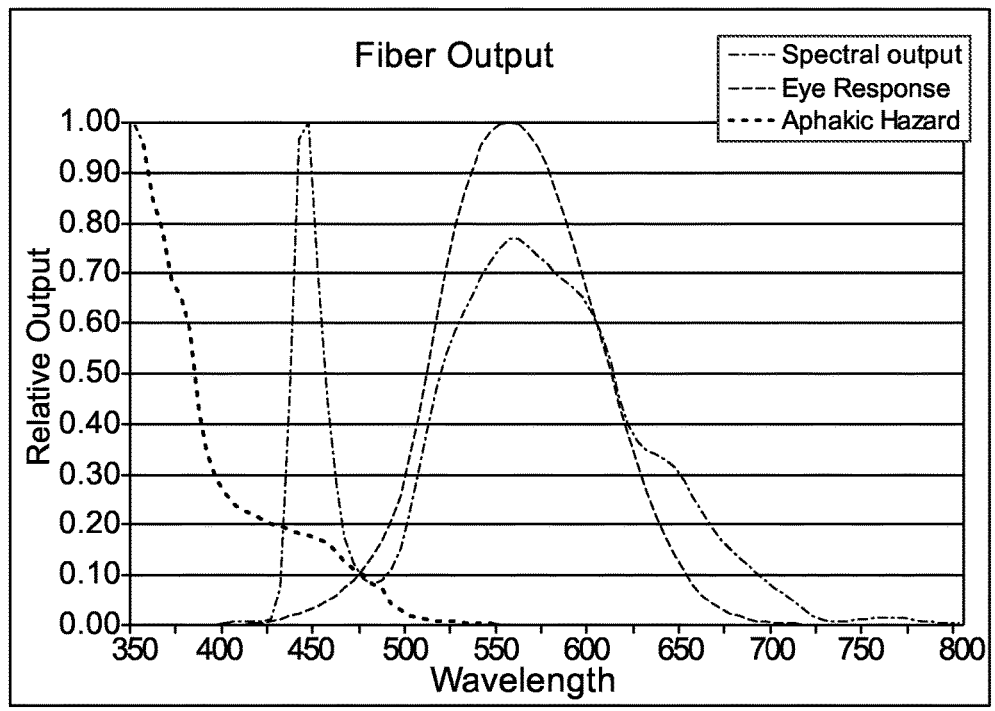
FIG. 12C illustrates the relative spectral output of filtered LED light in the example illumination system of FIG. 12A.

The LED 1205 includes a flat window that protects the diode surface but does not significantly affect the radiation pattern of the LED 1205. A lens 1206 gathers light from the LED 1205. The lens 1206, for example, is a plastic hybrid asphere with a numerical aperture (NA) of 0.63. The lens 1206 has a combination of aspheric and diffractive surfaces to reduce both chromatic and spherical aberration common to traditional lens designs. The light emitting surface of the LED 1205 is placed at the focal point of the lens 1206. Light exiting the lens 1206 is generally collimated. An absorptive filter 1208 is placed in the light column to tailor the spectral distribution. The filter 1208, for example, may be formed from Schott GG435 glass that is approximately 6 mm thick. The filter 1208 works in concert with the specific spectral output of the LED 1205. In other words, the specification for the filter 1208 may depend on the LED output spectrum. Consideration is given to color, phototoxicity, and luminous efficacy of the output spectrum during specification of the filter 1208. As a reference, the unfiltered output from the LED 1205 may measure 0.30, 0.28 CIE chromaticity, 625 lumens per hazardous watt, and 271 lumens per watt, while the filtered output may measure 0.36, 0.39 CIE chromaticity, 1951 lumens per hazardous watt, and 363 lumens per watt. All of which are much more desirable for an ophthalmic light source. FIG. 12C illustrates the relative spectral output of the filtered LED light.

A second lens 1210, which is substantially similar to the collimating lens 1206, gathers the filtered light and focuses it to an image of the LED 1205. The proximal end of an optical fiber 1202 is placed at the focal point of the second lens 1210 to guide the light to the surgical field.

Output power from the LED 1205 may be sensitive to temperature. As operating current is increased, die temperature also tends to increase. As die temperature increases, the output light level at a fixed drive current tends to decrease relative to the same drive current at lower temperature. The PCB 1203 to which the LED 1205 is mounted maximizes heat removal from the LED 1205. The board, for example, may be formed from approximately 0.38 mm (0.015 inch) thick fiberglass with copper traces (for signals and power) located on the top (LED) side of the board. Plated through-holes provide attachment points to solder the PCB 1203 to a copper base plate 1209, e.g., having a thickness of approximately 3.175 mm (0.125 inch). The copper base plate 1209 has a copper post of approximately 0.38 mm (0.015 inch) that protrudes through a hole in the PCB 1203 to provide direct contact between the central contact of the LED 1205 and the copper base plate 1209. The central contact of the LED 1205 is provided to allow heat to be conducted away from the light emitting die. This configuration allows the heat from the LED 1205 to quickly spread across a large area with minimal thermal resistance. The copper base plate 1209 is mounted to a Peltier cooler 1207. The Peltier cooler 1207 pumps heat from the copper base plate 1209 to an aluminum post 1204 to which the cooler 1207 is mounted. The amount of heat that is pumped relates to the amount of drive current given to the Peltier cooler 1207. The aluminum post 1204 is mounted to a multi-finned aluminum heat sink. The heat sink efficiently transfers heat to cooling air that is blown across it by that fan that is also mounted onto the heat sink. A thermistor is mounted on the PCB 1203 with a direct connection to the copper post to monitor LED temperature. Control electronics use the signal from the thermistor to adjust the Peltier cooler 1207 current and control temperature of the LED 1205.

As described above, aspects of the present invention provide systems and methods for driving a vitrector, providing aspiration, and handling fluid-air exchange in a vitrectomy system without relying on special power and gas systems. For example, aspects of the present invention use gas more efficiently so that the vitrectomy system can use widely available and smaller gas cylinders. Thus, corresponding embodiments are portable and may be used in a variety of clinical environments.

While the present invention has been described in connection with a number of exemplary embodiments, and implementations, the present inventions are not so limited, but rather cover various modifications, dimensions, shapes, and equivalent arrangements. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only. For example, although embodiments described above may be indicated for vitreous biopsy and vitreous taps, aspects of the present invention may be applied in other procedures, such as floaterectomies and blood removal.

What is claimed is:

1. A system for conducting a vitrectomy, the system comprising:
   a vitrector including a cutting mechanism that opens and closes according to a pressure and a resisting force at the vitrector; and
   a pulse-generating system generating pulses at the vitrector, the pulses causing the pressure at the vitrector to vary according to a cycle, the varying pressure and the resisting force at the vitrector causing the cutting mechanism of the vitrector to open and close,
   wherein, at a first time in the cycle, the pulse-generating system generates a pulse and raises the pressure at the vitrector to a maximum pressure to close the cutting mechanism, and
   at a second time in the cycle, the pulse-generating system reduces the pressure at the vitrector to a minimum pressure that is greater than ambient, the pressure at the vitrector being maintained at least at the minimum pressure and the resisting force causing the cutting mechanism to open.

2. The system of claim 1, wherein the pulse-generating system includes a first valve and a second valve, the first valve and the second valve being operable to raise and reduce the pressure at the vitrector according to the cycle.

3. The system of claim 1, wherein the pulse-generating system includes a first two-way valve and a second two-way valve, the first two-way valve being coupled to a gas source and to the vitrector, and the second two-way valve being coupled to the vitrector and to atmosphere.

4. The system of claim 3, wherein, at the first time in the cycle, the first two-way valve opens for a first period of time to raise the pressure at the vitrector to the maximum pressure, the maximum pressure being equal to a first threshold pressure to close the cutting mechanism of the vitrector, and, at the second time in the cycle, the second two-way valve opens for a second period of time to reduce the pressure at the vitrector to the minimum pressure, the minimum pressure being equal to a second threshold pressure to allow the cutting mechanism to open.

5. The system of claim 4, wherein the second two-way valve opens after a delay after the first two-way valve closes.

6. The system of claim 1, wherein the pulse generating system is configured to receive gas from a gas source, the gas source being a portable gas canister having a size of approximately 12 g to 33 g.

7. The system of claim 1, wherein the vitrector is configured to receive gas through tubing, the tubing being maintained at at least at the minimum pressure.

8. The system of claim 7, wherein the tubing has a given length, and for the given length, the tubing has a selected inner diameter that minimizes air flow while allowing the vitrector to operate at a range of selectable cut speeds.

9. A method for virectomy, comprising:
   providing a pulse-generating system; and
   generating pulses from the pulse-generating system at a vitrector, the vitrector including a cutting mechanism, the pulses causing the pressure at the vitrector to vary according to a cycle, the varying pressure and a resisting force at the vitrector causing the cutting mechanism of the vitrector to open and close, the act of generating pulses including:
      raising, at a first time in the cycle, the pressure at the vitrector to a maximum pressure by the generation of a pulse by the pulse-generating system to close the cutting mechanism, and
      reducing, at a second time in the cycle, the pressure at the vitrector to a minimum pressure that is greater than ambient, the pressure at the vitrector being maintained at least at the minimum pressure and the resisting force causing the cutting mechanism to open.

10. The method of claim 9, wherein the pulse-generating system includes a first valve and a second valve, the first valve and the second valve being operable to raise and reduce the pressure at the vitrector according to the cycle.

11. The method of claim 9, wherein the pulse-generating system includes a first two-way valve and a second two-way valve, the first two-way valve being coupled to a gas source and to the vitrector, and the second two-way valve being coupled to the vitrector and to atmosphere.

12. The method of claim 11, wherein the act of generating pulses includes:
   at the first time in the cycle, opening the first two-way valve for a first period of time to raise the pressure at the vitrector to the maximum pressure, the maximum pressure being equal to a first threshold pressure to close the cutting mechanism of the vitrector, and
   at the second time in the cycle, opening the second two-way valve for a second period of time to reduce the pressure at the vitrector to the minimum pressure, the minimum pressure being equal to a second threshold pressure to allow the cutting mechanism to open.

13. The method of claim 12, wherein the act of generating pulses includes opening the second two-way valve opens after a delay of approximately 8 ms after the first two-way valve closes.

14. The method of claim 9, wherein the pulse generating system is configured to receive gas from a gas source, the gas source being a portable gas canister having a size of approximately 12 g to 33 g.

15. The method of claim 9, wherein the vitrector is configured to receive gas through tubing, the tubing being maintained at at least at the minimum pressure.

16. The method of claim 15, further comprising wherein the tubing has a given length, and for the given length, the tubing has a selected inner diameter that minimizes air flow while allowing the vitrector to operate at a range of selectable cut speeds.

17. A system for conducting a vitrectomy, comprising:
a vitrector including a cutting mechanism that opens and closes according to a pressure at the vitrector; and
a pulse-generating system generating pulses at the vitrector, the pulses causing the pressure at the vitrector to vary according to a cycle, the cycle including only a single pulse, the varying pressure at the vitrector causing the cutting mechanism of the vitrector to open and close,
wherein, at a first time in the cycle, the pulse-generating system generates the single pulse and raises the pressure at the vitrector to a maximum pressure, and
at a second time in the cycle, the pulse-generating system reduces the pressure at the vitrector to a minimum pressure that is greater than ambient, the pressure at the vitrector being maintained at least at the minimum pressure.

* * * * *